US012582642B2

(12) United States Patent
Onogi et al.

(10) Patent No.: US 12,582,642 B2
(45) Date of Patent: Mar. 24, 2026

(54) COMPOSITION FOR TREATING, IMPROVING, AND/OR PREVENTING PROGRESSION OF BOVINE PAPILLOMATOSIS CAUSED BY BOVINE PAPILLOMAVIRUS

(71) Applicant: KinoPharma, Inc., Tokyo (JP)

(72) Inventors: Hiroshi Onogi, Tokyo (JP); Tomas Javier Acosta Ayala, Hokkaido (JP)

(73) Assignee: KINOPHARMA, INC., Tokyo (JP)

( * ) Notice: Subject to any disclaimer, the term of this patent is extended or adjusted under 35 U.S.C. 154(b) by 679 days.

(21) Appl. No.: 17/928,848

(22) PCT Filed: May 28, 2021

(86) PCT No.: PCT/JP2021/020456
§ 371 (c)(1),
(2) Date: May 2, 2023

(87) PCT Pub. No.: WO2021/246332
PCT Pub. Date: Dec. 9, 2021

(65) Prior Publication Data

US 2024/0285602 A1 Aug. 29, 2024

(30) Foreign Application Priority Data

Jun. 2, 2020 (JP) ................................. 2020-096375

(51) Int. Cl.

| | |
|---|---|
| ***A61K 31/4545*** | (2006.01) |
| ***A61K 9/06*** | (2006.01) |
| ***A61K 9/70*** | (2006.01) |
| ***A61P 17/02*** | (2006.01) |

(52) U.S. Cl.
CPC ............ *A61K 31/4545* (2013.01); *A61K 9/06* (2013.01); *A61K 9/7015* (2013.01); *A61P 17/02* (2018.01)

(58) Field of Classification Search
CPC ............................ A61K 31/4545; A61P 17/02
See application file for complete search history.

(56) References Cited

U.S. PATENT DOCUMENTS

| | | | |
|---|---|---|---|
| 2007/0135367 | A1 | 6/2007 | Hagiwara et al. |
| 2021/0100781 | A1 | 4/2021 | Hagiwara et al. |

FOREIGN PATENT DOCUMENTS

| | | | |
|---|---|---|---|
| JP | 2006-050911 | A | 2/2006 |
| JP | 2006-129795 | A | 5/2006 |
| JP | 2016-036340 | A | 3/2016 |
| WO | 2005/063293 | A1 | 7/2005 |
| WO | 2009/020198 | A1 | 2/2009 |

OTHER PUBLICATIONS

Munday (Veterinary Pathology, 2014, vol. 51, No. 6, p. 1063-1075) (Year: 2014).*
Extended European Search Report issued in corresponding European Patent Application No. 21816967.0 dated May 21, 2024.
Yamamoto et al., "CDK9 inhibitor FIT-039 prevents replication of multiple DNA viruses," The Journal of Clinical Investigation, 124 (8): 3479-3488 (2014).
Sumi et al., "Safety and plasma Concentrations of a Cyclin-dependent Kinase 9 (CDK9) Inhibitor, FIT039, Administered by a Single Adhesive Skin Patch Applied on Normal Skin and Cutaneous Warts," Clinical Drug Investigation, 39 (1): 55-61 (2019).
Tong et al., The bovine papillomavirus E6 oncoprotein interacts with paxillin and disrupts the actin cytoskeleton, Proceedings of the National Academy of Sciences, 94 (9): 4412-4417 (1997).
International Search Report issued in corresponding International Patent Application No. PCT/JP2021/020456 dated Jul. 13, 2021.

* cited by examiner

*Primary Examiner* — James D. Anderson
(74) *Attorney, Agent, or Firm* — Morgan, Lewis & Bockius LLP

(57) ABSTRACT

Provided are a composition for treatment and the like of bovine papillomatosis caused by bovine papillomavirus, and a method using the same. Provided are a composition for treatment, amelioration, and/or suppressing the progression of bovine papillomatosis caused by bovine papillomavirus, the composition containing, as an active ingredient, a compound represented by Formula (I) below or a pharmaceutically acceptable salt of the compound; and a method for treating, ameliorating, and/or suppressing progression of, bovine papillomatosis caused by bovine papillomavirus, the method including administering, to a cow, a compound represented by Formula (I) below or a pharmaceutically acceptable salt of the compound:

(I)

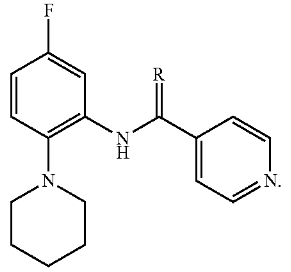

9 Claims, 2 Drawing Sheets

COMPOSITION FOR TREATING, IMPROVING, AND/OR PREVENTING PROGRESSION OF BOVINE PAPILLOMATOSIS CAUSED BY BOVINE PAPILLOMAVIRUS

FIELD

The present disclosure relates to a composition for treatment, amelioration, and/or suppression of progression of bovine papillomatosis caused by bovine papillomavirus (BPV), and relates to a method for treating, ameliorating, and/or suppressing progression of, bovine papillomatosis caused by BPV in cows, using the above-mentioned composition.

BACKGROUND

Papillomatosis is a disease caused by infection with papillomavirus (PV) in epithelium or mucous membrane, which forms a benign tumor (wart) that is called a papilloma in the site of infection. Known as mammals that can be infected with papillomavirus are humans, cows, horses, dogs, cats, and yaks. Among PVs of mammals other than humans, BPV is known best.

BPV infects skins or some mucous membranes of cows, thereby causing bovine papillomatosis. Bovine papillomatosis often occurs in young cows, and develops symptoms very frequently. They are however generally benign tumors and most of them are naturally healed, which has made bovine papillomatosis scarcely considered as a serious problem. When a lesion of a papilloma is formed in a teat area of a dairy cow, however, the lesion can obstruct milking or cause a secondary bacterial infection leading to mastitis in some cases. Influences of spread of BPV infection, such as the spreading of teat papillomatosis over a whole farm via a milking machine for dairy cows, has been reported in recent years.

As a method for treating a papilloma of a cow, the following have been attempted: surgically removing a papilloma; detoxicating ground wart and injecting the same; mixing shelled adlay in fodder to let cows take the same; and applying pyroligneous acid to a diseased part.

The applicant et al. propose an antiviral agent against viral infectious diseases caused by human papillomavirus (HPV) (Patent Document 1).

CITATION LIST

Patent Literature

[Patent Literature 1] WO2009/020198

SUMMARY

Technical Problem

It can be said that no fundamental therapeutic method for treating bovine papillomatosis is available, although problems have been caused by bovine papillomatosis, as described above. Therefore, a method for treating bovine papillomatosis has been desired.

Solution to Problem

The present disclosure, in one aspect, relates to a composition for treatment, amelioration, and/or suppression of progression of bovine papillomatosis caused by bovine papillomavirus, the composition containing, as an active ingredient, a compound represented by Formula (I) below or a pharmaceutically acceptable salt of the compound:

(I)

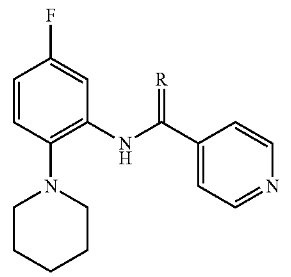

where R represents an oxygen atom or a sulfur atom.

The present disclosure, in one aspect, relates to a method for treating, ameliorating, and/or suppressing progression of, bovine papillomatosis caused by bovine papillomavirus, the method including administering, to a cow, a composition containing a compound represented by Formula (I) above or a pharmaceutically acceptable salt of the compound.

Advantageous Effects of Invention

The present disclosure, in one aspect, can provide a composition that is capable of treating, ameliorating, and/or suppressing the progression of, bovine papillomatosis caused by BPV, and can provide a method that is capable of treating, ameliorating, and/or suppressing progression of the bovine papillomatosis using the above-mentioned composition.

DESCRIPTION OF EMBODIMENTS

Figure 1A:
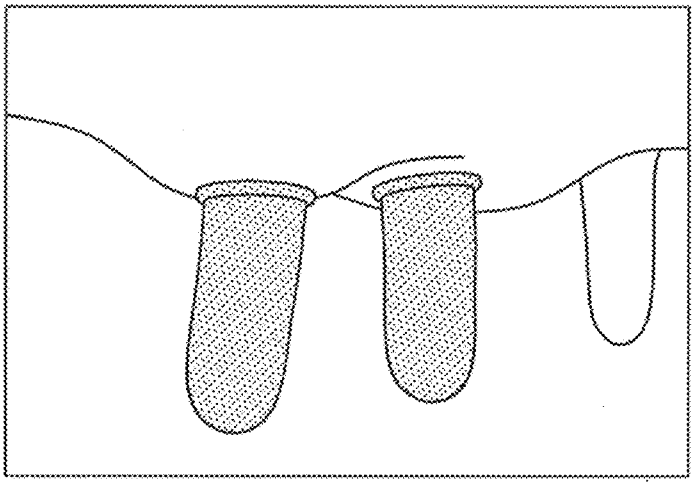
FIGS. 1(*a*) to 1(*d*) illustrate shapes of teat covering containers and covering materials in one embodiment.
Figure 1B:
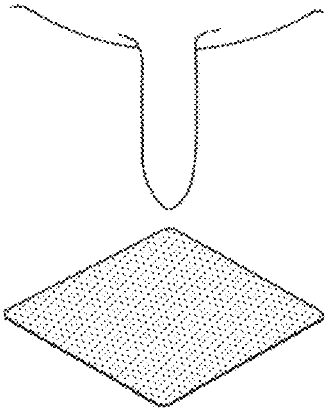
Figure 1C:
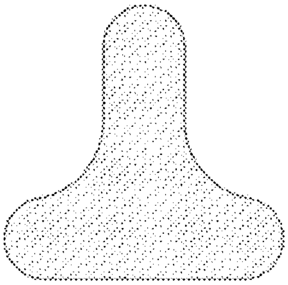
Figure 1D:
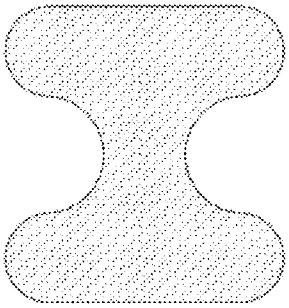

As described above, PV is a virus that has many various virus types found from various animals such as cows, horses, cats, dogs, and humans, and that is widely spread in the world. PV is of great variety, and the genotype and condition of PV vary depending on a species (host animal) that the PV infects. Besides, PV generally has high species specificity, and it is considered that normally the infection of PV does not cross the boundary between species. In particular, the target that BPV infects is a cow, and a human cannot be infected with BPV. Likewise, a cow cannot be infected with HPV.

BPV is a papillomavirus that specifically infects a cow and causes a bovine papilloma. As a method for treating bovine papillomatosis caused by BPV, a method of detoxicating ground wart and injecting the same, feeding shelled adlay, and application of pyroligneous acid to a diseased part have been attempted, in addition to surgical removal or removal of a lesion part by freezing. In a case of surgical removal, however, the recurrence rate is high. Sufficient effects cannot seem to be achieved by the other methods, either.

The present disclosure is based on the following findings: although it has been considered that a compound that is proposed to be used in a vaccine or a therapeutic method against cervical cancer of a human caused by HPV, that is, an antiviral agent against HPV disclosed in Patent Document 1, would not have therapeutic effects against bovine papillomatosis caused by BPV, because of the high species specificity of the same, it was found to have unexpected effects on bovine papillomatosis caused by BPV.

The present disclosure is based on the findings that a compound represented by the formula shown below, N-[5-fluoro-2-(1-piperidinyl)phenyl]-4-pyridinethioamide, having an antiviral effect, when being applied on a bovine papilloma (wart) caused by BPV, can exhibit an excellent effect of suppressing the growth of the papilloma (wart) already formed, and further, an excellent effect of disappearance or size reduction of a wart:

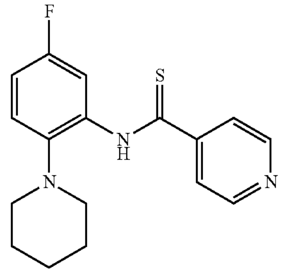 [SMILES: Fc1ccc(N2CCCCC2)c(NC(=S)c2ccncc2)c1]

The "treatment, amelioration, and/or suppression of progression of bovine papillomatosis" in the present disclosure, in one or a plurality of embodiments, is the suppression of the size increase of a papilloma (wart) already formed, the disappearance of a wart, or the size reduction of a wart, achieved by administering an agent (composition) of the present disclosure to a target.

"Bovine papillomatosis caused by BPV" in the present disclosure, in one or a plurality of embodiments, refers to a disease of a cow infected with BPV, forming a papilloma at a site of infection. In one or a plurality of embodiments, bovine papillomatosis caused by BPV is bovine papillomatosis, bovine cutaneous papillomatosis, bovine teat papillomatosis, and sarcoid (fibropapillomatosis). In one or a plurality of particularly non-limiting embodiments, a site of infection (detected lesion) is a teat, a skin, or an alimentary canal (the oral cavity, the esophagus, or the like).

[Composition for Treatment, Amelioration, and/or Suppression of Progression of Papillomatosis]

The present disclosure, in one aspect, can provide a composition for treatment, amelioration, and/or suppression of progression of bovine papillomatosis caused by BPV, the composition containing, as an active ingredient, a compound represented by Formula (I) below or a pharmaceutically acceptable salt of the compound. In one or a plurality of embodiments, the compound represented by Formula (I) may have an anti-DNA virus effect and/or an anti-RNA virus effect.

(I)

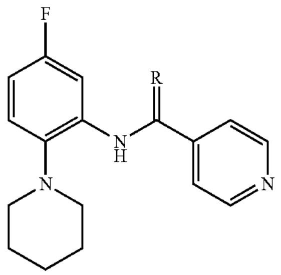

In Formula (I), R represents an oxygen atom or a sulfur atom.

In one or a plurality of embodiments, the compound represented by Formula (I) in the present disclosure is N-[5-fluoro-2-(1-piperidinyl)phenyl]-4-pyridinethioamide (Compound A), and N-[5-fluoro-2-(1-piperidinyl)phenyl]-4-pyridinecarboxyamide (Compound B) represented by the following formulae:

Compound A

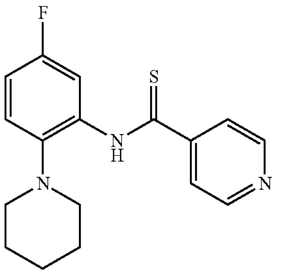

Compound B

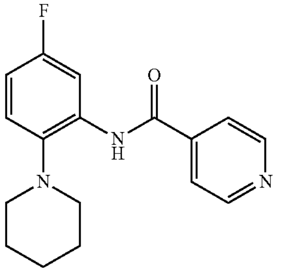

In one or a plurality of embodiments, the compounds represented by Formula (I) can be produced by a known producing method or with reference to WO2009/020198.

In the present disclosure, the "pharmaceutically acceptable salt" is a pharmacologically and/or pharmaceutically acceptable salt. It is, for example, an inorganic acid salt, an organic acid salt, an inorganic base salt, an organic base salt, an acidic amino acid salt, or a basic amino acid salt. In one or a plurality of embodiments, the inorganic acid salt is a hydrochloride, a hydrobromide, a sulfate, a nitrate, or a phosphate. In one or a plurality of embodiments, the organic acid salt is an acetate, a succinate, a fumarate, a maleate, a tartrate, a citrate, a lactate, a stearate, a benzoate, a methanesulfonate, or a p-toluenesulfonate. In one or a plurality of embodiments, the inorganic base salt is a salt of an alkali metal such as a sodium salt or a potassium salt, an alkali earth metal salt such as a calcium salt or a magnesium salt, an aluminum salt, or an ammonium salt. In one or a plurality of embodiments, the organic base salt is a diethylamine salt, a diethanolamine salt, a meglumine salt, or an N,N'-dibenzylethylenediamine salt. In one or a plurality of embodiments, the acidic amino acid salt is an aspartate, or a glutamate. In one or a plurality of embodiments, the basic amino acid salt is an arginine salt, a lysine salt, or an ornithine salt.

In the present disclosure, the "salt of a compound" may encompass a hydrate that can be formed when the compound absorbs moisture. Further, in the present disclosure, the "salt of a compound" may also encompass a solvate that can be formed when the compound absorbs a solvent of another kind.

In one or a plurality of embodiments, the composition of the present disclosure contains the above-described compound as an active ingredient, and may further contain a pharmaceutically acceptable carrier, preservative, diluent, or excipient, or another pharmaceutically acceptable component.

In one or a plurality of embodiments, the composition of the present disclosure can be systemically and/or locally effective. In one or a plurality of embodiments, the composition of the present disclosure can be administered orally, parenterally, transcutaneously, transmucosally, pernasally, through a buccal route, through a rectum route, a tongue route, transdermally, or through a conjunctiva route. The composition of the present disclosure is preferably locally administered, and more preferably transcutaneously administered.

In one or a plurality of embodiments, the composition of the present disclosure may have a dosage form suitable for an administration route by using the known formulation technology.

In one or a plurality of embodiments, regarding the oral administration form, the pharmaceutical composition can be administered in such a dosage form as a tablet, a capsule, a granule agent, a powder, a pill, a troche, a pellet, a syrup, a suspension, a liquid formulation, or an aerosol.

In one or a plurality of embodiments, regarding the non-oral administration form, the pharmaceutical composition can be administered in such a dosage form as an ointment, a cream, an injection agent, a liquid formulation or an immersion agent, an aerosol, a spray, a suppository agent, a plaster agent, poultice agent, a lotion agent, or a liniment agent.

The composition of the present disclosure may be stored and used after being prepared in a dosage form to be administered to a teat, or alternatively, may be prepared at time of use. Either of these may be chosen appropriately depending on the use status and the intended purpose of use.

In one or a plurality of embodiments, the composition of the present disclosure can be produced by a known method using an additive and the like. Examples of the additive include excipients, lubricants, binders, disintegrators, stabilizers, corrigents, and diluents. The composition of the present disclosure may contain an additive such as a surfactant and a pH adjuster other than the above-described additives.

The composition of the present disclosure can be produced by using a surfactant or an emulsifier as required. When the composition of the present disclosure is in a dosage form using a solvent such as a liquid agent or an immersion agent, any of an aqueous solvent, a non-aqueous solvent, and a mixture solvent obtained by mixing a non-aqueous solvent and an aqueous solvent can be used as the solvent, among which an aqueous solvent, or a mixture of a non-aqueous solvent and an aqueous solvent in which the aqueous solvent is principal, is preferred. As these aqueous solvent and non-aqueous solvent, various solvents are known, and any can be appropriately selected based on the administration route and the dosage form, with reference to known information. In addition, a target drug formulation can be produced by using any of these solvents, as well as a surfactant or an emulsifier as required.

In one or a plurality of embodiments, the composition of the present disclosure has a content of the compound expressed by Formula (I), as an active ingredient, of 0.01% by weight to 50% by weight, or 0.1% by weight to 20% by weight. The dosage amount of the composition of the present disclosure can be appropriately selected according to the dosage form and the administration route. The dosage amount of the composition of the present disclosure in a local administration case can be appropriately set according to the size, range, and the like of a wart. In one or a plurality of embodiments, the composition is administered so that the amount of the active ingredient in the composition is about 0.01 mg/wart to 40 mg/wart. When the composition of the present disclosure is applied to a teat, for example, though the case is not limited to this, the composition is administered so that the applied amount of the active ingredient in the composition is 0.01 $mg/cm^2$ to 40 $mg/cm^2$, preferably 0.1 $mg/cm^2$ to 20 $mg/cm^2$, and more preferably 0.3 $mg/cm^2$ to 6 $mg/cm^2$ with respect to the area of the teat surface. Regarding the dosage amount of the composition of the present disclosure in an oral administration case or an injection case, in one or a plurality of embodiments, the composition is administered so that the amount of the active ingredient in the composition is about 0.01 mg/kg (body weight) to 100 mg/kg (body weight).

When the composition of the present disclosure is locally administered to a teat, or is administered by application to a teat, the entirety of the teat to which the composition of the present disclosure has been administered or applied, or the part thereof to which it has been administered or applied, is preferably covered. Covering the entirety of the teat or the part thereof makes the administration or penetration of the active ingredient to the diseased part more effective. As the cover of the teat part, any material that can cover the teat can be used without any particular limitation, and, for example, a teat covering container or a covering material can be used. Examples of the teat covering container include, though not limited to, a teat-shaped container made of an elastic material (for example, a sac). As the elastic material, any elastic polymer material that is commonly used can be used without any particular limitation, and it is preferably a material that has less stimulation to a teat. In addition, to keep a teat with a diseased part in a good state, a material that does not allow the composition of the present disclosure to leak out but has breathability is preferred. Examples of such a material include, though not limited to, natural rubber materials, silicon materials, and latex materials. As a teat covering material, any material that forms a coating film after the material is applied over a teat can be used without any particular limitation, and it is preferably a covering material made of a component that has less stimulation to a teat. Examples of such a coating material include, though not limited to, a composition (coating agent) composed of a natural component that can form a coating when being applied to a skin of a teat or the like, or a composition composed of a mixture of such natural components. These covering materials may be applied or sprayed over a teat to which the composition of the present disclosure is administered or applied, thereby forming a coating there. The coating thus formed preferably does not allow the composition of the present disclosure to leak out but has breathability.

Alternatively, in one or a plurality of embodiments, the composition of the present disclosure may be applied to a teat protecting container or a covering material in advance so that a teat is covered with the same, whereby the composition of the present disclosure can be administered to a cow.

FIGS. 1(*a*) to 1(*d*) illustrate teat covering containers and covering materials in one embodiment. FIG. 1(*a*) illustrates a state of teats of a cow covered with teat covering containers each of which is composed of a cylindrical sac (in a finger sack shape). FIGS. 1(*b*) to 1(*d*) illustrate exemplary shapes of a teat covering material in a pad (patch or sheet) form. The shape of the teat covering material may be a quadrilateral (FIG. 1(*b*)), an anchor shape (FIG. 1(*c*)), or an H-letter shape (FIG. 1(*d*)). In one or a plurality of embodiments, the teat covering material, as illustrated in FIG. 1(*b*), may be attached in such a manner that the center of the teat covering material is brought into contact with a tip of a teat of a cow and in this state the teat covering material covers the whole teat, whereby the teat covering material can cover the teat.

The composition of the present disclosure is preferably used together with a teat covering container or a covering material. By administering or applying the composition to a teat and thereafter covering the teat with a teat covering container or a covering material, the administration or penetration of an active ingredient is made more effective. The present disclosure also encompasses a composition of the present disclosure that is characterized by being used together with a teat covering container or a covering material. Further, the present disclosure also encompasses a combination of a composition of the present disclosure with a teat covering container or a covering material. Such a combination may be provided in a set or a kit. The composition of the present disclosure also can be administered to a cow by applying the composition over an inner side of a teat covering container in advance and putting the container on a teat. The present disclosure also encompasses such a teat covering container having the composition of the present disclosure applied over an inner side thereof.

The composition of the present disclosure can be used in the treatment, amelioration, and/or suppression of progression of bovine papillomatosis caused by BPV in a cow. When a teat has a lesion of papilloma, in one or a plurality of embodiments, the composition of the present disclosure may be applied to the teat with the lesion, thereby causing the suppression of growth of a papilloma formed in the teat, the size reduction of a papilloma, and/or the disappearance of a papilloma to occur. In one or a plurality of embodiments, therefore, by administering the composition of the present disclosure to a dairy cow, the obstruction of milking, caused by a papilloma formed in a teat, can be prevented. When a teat has a lesion of a papilloma, in one or a plurality of embodiments, the composition of the present disclosure may be applied over an entirety of a teat with the papilloma (wart), or alternatively, it may be applied only to the papilloma (wart) formed in the teat. The administration route, however, is not limited to these. The composition may be administered orally, or by injection.

[Method for Treatment, Amelioration, and/or Suppression of Progression of Papillomatosis]

The present disclosure, in another aspect, relates to a method for treating, ameliorating, and/or suppressing progression of bovine papillomatosis caused by BPV in a cow. The method of the present disclosure includes administering, to a cow as a target, a composition containing a compound represented by Formula (I) above or a pharmaceutically acceptable salt of the compound.

In the present aspect, papillomatosis, active ingredients, a pharmaceutical composition, a method for using the same, and the like, may be set as described above.

The present disclosure may relate to one or a plurality of embodiments described below:

[1] A composition for treatment, amelioration, and/or suppression of progression of bovine papillomatosis caused by bovine papillomavirus, the composition containing, as an active ingredient, a compound represented by Formula (I) below or a pharmaceutically acceptable salt of the compound:

(I)

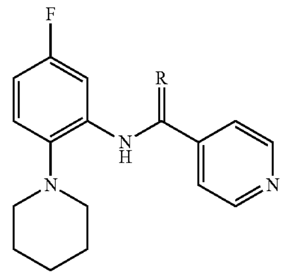

where R represents an oxygen atom or a sulfur atom.

[2] The composition according to [1], wherein the compound represented by Formula (I) is a compound represented by the following formula or a pharmaceutically acceptable salt of the compound:

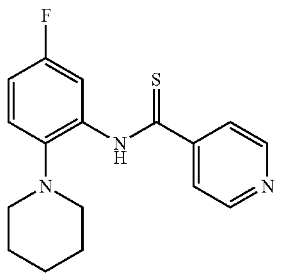 [SMILES: Fc1ccc(N2CCCCC2)c(NC(=S)c2ccncc2)c1]

[3] The composition according to [1] or [2], wherein the papillomatosis is bovine teat papillomatosis.

[4] The composition according to any one of [1] to [3], the composition being a topical composition to be applied to a teat of a dairy cow.

[5] A method for treating, ameliorating, and/or suppressing progression of bovine papillomatosis caused by bovine papillomavirus, the method including administering, to a cow, a composition containing, as an active ingredient, a compound represented by Formula (I) below or a pharmaceutically acceptable salt of the compound:

(I)

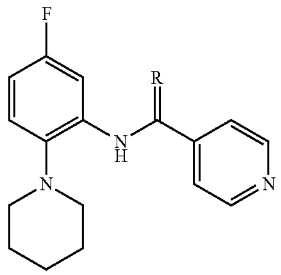

where R represents an oxygen atom or a sulfur atom.

[6] The method according to [5], wherein the cow is a dairy cow, and the papillomatosis is bovine teat papillomatosis, the method including applying the composition to a teat of the dairy cow.

EXAMPLE

Hereinafter, although the following description describes the present disclosure in more detail by way of examples, these are illustrative, and the present disclosure is not limited to these examples. Note that all of the references cited in the present disclosure is incorporated as a portion of the present disclosure.

Production Example 1: Production of N-[5-fluoro-2-(1-piperidinyl)phenyl]-4-pyridinethioamide (Compound A)

Compound A represented by the following chemical formula was produced with reference to Reference Example 11 of WO2009/020198:

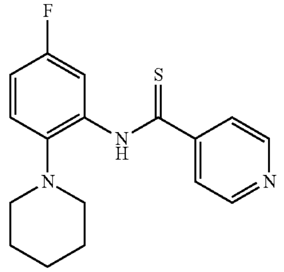

Production Example 2: Preparation of Ointment Agent Containing Compound A

Compound A, 120 mg, was dissolved in an ointment agent (white petrolatum), 3880 mg that was heated to 60° C. in advance to be molten, and the mixture was agitated at 60° C. till it became homogeneous, whereby an ointment agent (Compound A: 3% by weight) was prepared.

[Therapeutic Effect Confirmation Test Performed on Dairy Cow Having Papilloma]

To female dairy cows (four), each having papillomas in both of front teats, an ointment agent containing Compound A was applied once a day to a papilloma (wart) of one of the front teats (test section). A dressing tape (Navis, PROSHARE Dressing Role, No. 8-5965-01) was applied around the teat after the application of the ointment agent to prevent external contamination. The ointment agent was applied over a surface of the teat at about 0.01 g to about 0.2 g (equivalent to the active ingredient of about 0.3 mg to about 6 mg) per 1 $cm^2$ of the surface area. The application (treatment) of 5-day administration with 2-day rest was continued for 4 weeks. The diseased part was imaged once a week. Pharmaceutical effects were evaluated based on a state of the diseased part (wart) four weeks after the start of the application.

As a control, an ointment base that did not contain Compound A was applied to a wart of the other teat, which was not a test section (control section).

[Evaluation Method 1]

Changes (size reduction/disappearance, no change, and growth/occurrence) of warts after four-week administration were evaluated with the following three-level evaluation scores. No change" includes the suppression of growth and being non-effective. "Occurrence" means that a new wart was generated during the four-week administration.

Size reduction/disappearance=+1, no change=0, and growth/occurrence=−1.

The results are shown in Table 1 below.

TABLE 1

| Cow individual ID No. | Test section Size reduction/ Disappearance | Test section Growth/ Occurrence | Control section Size reduction/ Disappearance | Control section Growth/ Occurrence |
|---|---|---|---|---|
| 01 | +1 | 0 | +1 | 0 |
| 02 | +3 | −6 | +1 | −5 |
| 03 | +1 | 0 | 0 | −5 |
| 04 | +2 | 0 | 0 | 0 |
| Total | +7 | −6 | +2 | −10 |

Further, scores were added for each individual cow, and pharmaceutical effects for each individual cow were determined based on the following criteria.

Effective: Test section>Control section

Ineffective: Test section≤Control section

The results are shown in Table 2 below.

TABLE 2

| Cow individual ID No. | Determination | Effectiveness score Test section | Effectiveness score Control section |
|---|---|---|---|
| 01 | Ineffective | +1 | +1 |
| 02 | Effective | −3 | −4 |
| 03 | Effective | +1 | −5 |
| 04 | Effective | +2 | 0 |
| Total | Effective in three out of four cases | +1 | −8 |

In Table 1 above, the total score of the test sections was +1, and the total score of the control sections was −8. The ointment agent containing Compound A was therefore considered effective in the test sections.

In Table 2 above, regarding the evaluations of individual cows, effectiveness was observed in three cases out of four cases. The ointment agent containing Compound A was therefore considered effective.

Figure 2:
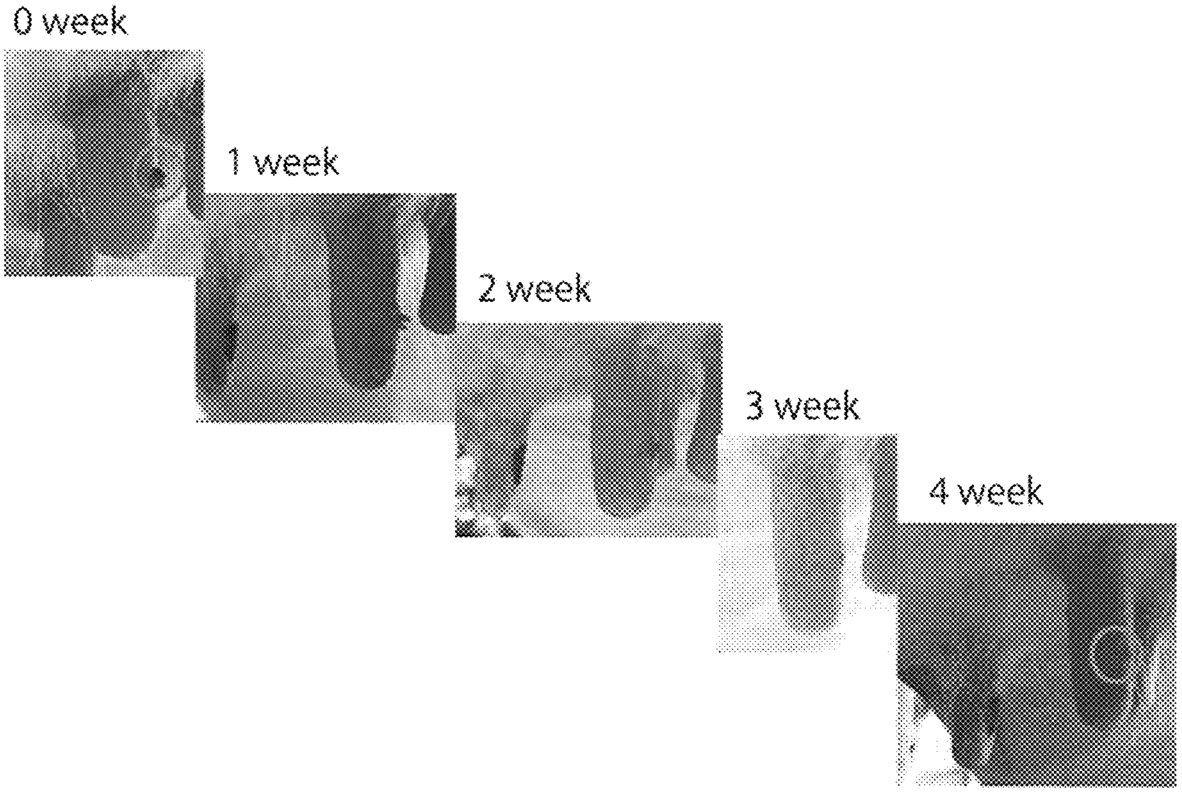
FIG. 2 shows an exemplary result of a pharmaceutical effect confirmation test on a compound A (N-[5-fluoro-2-(1-piperidinyl)phenyl]-4-pyridinethioamide).

FIG. 2 shows images of a diseased part in a test section (a case where warts disappeared) that were taken from before the start of administration to after the end of administration.

After the four-week administration, the administration was further continued under the same conditions for four weeks. As a result, sizes of additional four warts were reduced in the test section (two warts of these four disappeared).

[Evaluation Method 2]

When only small warts were targeted, the growth or size reduction of warts noticeably appear, which is considered to make it easier to determine the effects of Compound A. In view of this, only warts having a size of less than 5 mm before the application of an ointment agent were selected from the test sections and the control sections in the above-described confirmation test, and the ratio of warts that had smaller sizes or disappeared was calculated.

As a result, among the warts as analysis targets (14 warts in the test sections, 15 warts in the control sections), the ratio of warts that had smaller sizes or disappeared was 28.6% in the test sections, whereas the ratio was 0% in the control sections. Thus, clear effectivity by the ointment agent containing Compound A with respect to papillomas that occurred to cows was confirmed.

The invention claimed is:

1. A method for treating, ameliorating, and/or suppressing progression of bovine papillomatosis caused by bovine papillomavirus, the method comprising administering, to a cow in need thereof, a composition containing, as an active ingredient, a compound represented by Formula (I) below or a pharmaceutically acceptable salt of the compound:

(I)

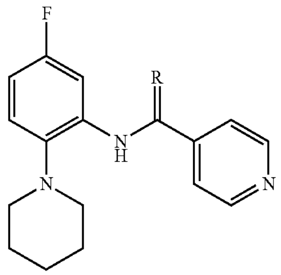

where R represents an oxygen atom or a sulfur atom.

2. The method according to claim 1, wherein the compound represented by Formula (I) is a compound represented by the following formula or a pharmaceutically acceptable salt of the compound:

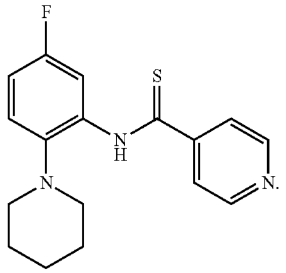 [SMILES: Fc1ccc(N2CCCCC2)c(NC(=S)c2ccncc2)c1]

3. The method according to claim 1, wherein the cow is a dairy cow, the papillomatosis is teat bovine papillomatosis, and the administering comprises applying the composition to a teat of the dairy cow.

4. The method according to claim 3, wherein the compound or the pharmaceutically acceptable salt of the compound is applied at 0.01 $mg/cm^2$ to 40 $mg/cm^2$ to a teat with a papilloma.

5. The method according to claim 3, further comprising, after applying the compound or the pharmaceutically acceptable salt of the compound to a teat, covering an applied site with a teat covering container or a covering material.

6. The method according to claim 5, wherein the teat covering container or the covering material is a container that covers a teat or a covering material that can form a coating film when being applied to a teat.

7. The method according to claim 1, wherein the cow is a dairy cow.

8. The method according to claim 1, wherein the papillomatosis is teat bovine papillomatosis.

9. The method according to claim 8, the administering comprises applying the composition to a teat of the cow.

* * * * *